United States Patent [19]

Gohbayashi et al.

[11] Patent Number: 4,885,382
[45] Date of Patent: Dec. 5, 1989

[54] METHOD OF PRODUCING TETRAKIS[3,5-DI-TERT-BUTYL-4-HYDROX-YPHENYL)PROPIONYLOXYMETHYL]ME-THANE

[75] Inventors: Masayoshi Gohbayashi, Nakatsu; Noritsugu Narita, Suzuka; Makoto Maruno, Mie, all of Japan

[73] Assignee: Yoshitomi Pharmaceutical Industries, Ltd., Osaka, Japan

[21] Appl. No.: 261,963

[22] PCT Filed: Feb. 1, 1988

[86] PCT No.: PCT/JP88/00087
§ 371 Date: Sep. 28, 1988
§ 102(e) Date: Sep. 28, 1988

[87] PCT Pub. No.: WO88/05772
PCT Pub. Date: Aug. 11, 1988

[30] Foreign Application Priority Data
Feb. 3, 1987 [JP] Japan ................... 62-24162

[51] Int. Cl.$^4$ ............................................. C07C 69/76
[52] U.S. Cl. .................................................. 560/75
[58] Field of Search ........................................ 560/75

[56] References Cited

U.S. PATENT DOCUMENTS

| | | | |
|---|---|---|---|
| 3,779,945 | 12/1973 | Dexter et al. | 560/75 |
| 4,396,552 | 8/1983 | Knobloch et al. | 560/75 |
| 4,511,491 | 4/1985 | Ishii et al. | 560/75 |
| 4,547,585 | 10/1985 | Yamanaka et al. | 560/75 |
| 4,594,444 | 6/1986 | Orban | 560/75 |
| 4,683,326 | 7/1987 | Orban et al. | 560/75 |
| 4,716,244 | 12/1987 | Orban et al. | 560/75 |

FOREIGN PATENT DOCUMENTS

| | | | |
|---|---|---|---|
| 9025349 | 2/1984 | Japan | 560/75 |
| 2201846 | 9/1987 | Japan | 560/75 |

*Primary Examiner*—Paul J. Killos
*Attorney, Agent, or Firm*—Wenderoth, Lind & Ponack

[57] ABSTRACT

A method for producing tetrakis[3-(3,5-di-tert-butyl-4-hydroxyphenyl)propionyloxymethyl]methane by ester exchange between a 3-(3,5-di-tert-butyl-4-hydroxyphenyl)propionic acid alkyl ester and pentaerythritol in the presence of a basic catalyst, which comprises carrying out the reaction in the presence of a 3-(3-tert-butyl-4-hydroxyphenyl)propionic acid alkyl ester.

According to the method of the invention, tetrakis[3-(3,5-di-tert-butyl-4-hydroxyphenyl)propionyloxymethyl]methane can be obtained in high yields as fine granules having good properties without coloration, with certainty and good reproducibility.

4 Claims, No Drawings

METHOD OF PRODUCING TETRAKIS[3,5-DI-TERT-BUTYL-4-HYDROXYPHENYL)PROPIONYLOXYMETHYL]METHANE

FIELD OF THE INVENTION

This invention relates to a method of producing tetrakis-[3-(3,5-di-tert-butyl-4-hydroxyphenyl)propionyloxymethyl]-methane [hereinafter sometimes referred to as "compound (I)"], which is in wide use as an antioxidant for polyolefins, among others, in the form of fine granules having good physical properties and in a purified form.

DESCRIPTION OF THE PRIOR ART

The compound (I) is commercially available in the form of white fine powders. However, such powders are still unsatisfactory from the transportation, handling, dosing and other viewpoints. For instance, they have a low bulk density, readily fly off into the air upon handling, are low in flowability and are difficult to adequately dose for extruder fusion mixing with polyolefins.

The most general method of producing the compound (I) comprises subjecting a 3-(3,5-di-tert-butyl-4-hydroxyphenyl)propionic acid alkyl ester [hereinafter sometimes referred to as "compound (II)"] and pentaerythritol to ester exchange (transesterification) reaction. Said method gives the compound (I) in relatively good yields. Japanese Patent Publication No. 19083/1967, for instance, discloses that the desired compound (I) is obtained as crystals having a melting point of 121°–122° C. when isopropanol is added to the product after said ester exchange reaction between the compound (II) and pentaerythritol and the resulting molecular adduct compound is isolated and recrystallized from heptane. Japanese Patent Publication No. 18617/1967 discloses that the compound (I) is obtained as a transparent, amber-colored, glassy substance having a softening point of 50°–60° C. when the ester exchange reaction product is purified by chromatography on neutral alumina using hexane as the eluent and the hexane is then removed. The latter further discloses, in another paragraph, that recrystallization of said reaction product from heptane gives crystals having a melting point of 119°–122° C. and recrystallization from cyclohexane gives crystals melting at 80°–90° C.

However, experiments conducted by the present inventors for checking these methods disclosed in the literature revealed that the compound (I) obtained still has those drawbacks which the above-mentioned commercial products have or that the compound (I) obtained is colored.

DISCLOSURE OF THE INVENTION

Accordingly, the present inventors conducted intensive investigations in an attempt to provide a method of producing the compound (I) in the form of fine granules having good physical properties and in a purified form without coloration by using the ester exchange reaction between the compound (II) and pentaerythritol and, as a result, have now completed the present invention.

Thus the invention provides a method of producing tetrakis[3-(3,5-di-tert-butyl-4-hydroxypenyl)propionyloxymethyl]methane by ester exchange between a 3-(3,5-di-tert-butyl-4-hydroxyphenyl)propionic acid alkyl ester and pentaerythritol in the presence of a basic catalyst, which comprises carrying out the reaction in the presence of a 3-(3-tert-butyl-4-hydroxyphenyl)propionic acid alkyl ester [hereinafter sometimes referred to as "compound (III)"].

In accordance with the invention, the step of ester exchange between the 3-(3,5-di-tert-butyl-4-hydroxyphenyl)propionic acid alkyl ester and pentaerythritol is to be followed by a purification step comprising recrystallization to give tetrakis[3-(3,5-di-tert-butyl-4-hydroxyphenyl)propionyloxymethyl]methane in a purified form. When said ester exchange reaction is carried out in the presence of 3(3-tert-butyl-4-hydroxyphenyl)propionic acid alkyl ester and in the presence of a basic catalyst as an ester exchange catalyst and when, in the purification step, the product from the ester exchange reaction step is purified by recrystallization from methanol and/or ethanol, the compound (I) can be obtained as fine granules with good physical properties.

As the alkyl ester compound (II), there may be mentioned straight or branched alkyl esters with 1–4 carbon atoms, preferably the methyl ester and ethyl ester, and mixtures thereof. The alkyl ester compound (III) is a straight or branched alkyl ester with 1–6 carbon atoms, such as methyl ester, ethyl ester, propyl ester, isopropyl ester, butyl ester, isobutyl ester, sec-butyl ester, tert-butyl ester, pentyl ester or hexyl ester; the methyl or ethyl ester is preferred from the industrial viewpoint, however.

The method of the invention produces the compound (I) as fine granules having good properties and in a purified form without coloration, with certainty and good reproducibility while making the best of the advantageous feature of the known method that the compound (I) can be obtained in high yields by subjecting the compound (II) and pentaerythritol to ester exchange. The amount of the compound (III) is minimal and therefore the purity and performance characteristics of the compound (I) are never impaired.

The reason why the compound (I) is obtained as fine granules with excellent properties when the method of the invention is applied is yet unclear. X-ray and other analyses indicate, however, that the compound (I) obtained by the method of the invention have the so-called beta crystal structure which is a reflection of high purity.

The objects and advantages of the invention will become more apparent from the more detailed description which follows.

In practicing the invention, an ester exchange reaction between the compound (II) and pentaerythritol in the presence of the above-mentioned compound (III) is carried out.

The compound (III) is used generally in an amount of about 0.1 to about 5.0% by weight, preferably in an amount of about 0.2 to about 1.0% by weight, relative to the compound (II). The presence of larger amounts of the compound (III) may reduce the yield of the compound (I), whereas smaller amounts of the compound (III) will fail to give the compound as fine granules having good properties.

The compound (III) should preferabley be present in the ester exchange reaction system from the beginning. Nevertheless, it is possible to add the compound (III) at an intermediate stage of the ester exchange reaction.

The compound (II) is preferably used in a stoichiometrically slight excess relative to pentaerythritol, namely in an amount of about 4.2–4.4 moles per mole of pentaerythritol.

In the ester exchange reaction step, an organotin compound is preferably used as a basic catalyst. Said organotin compound includes, among others, organotin oxides, such as monobutyltin oxide, dibutyltin oxide, tributyltin oxide and triphenyltin oxide; esters of organotin oxides, such as tributyltin phthalate and tributyltin acrylate; and organotin chlorides, such as monobutyltin trichloride, dibutyltin dichloride and tributyltin chloride. Among them, organotin oxides are preferred.

When used in amounts known to be sufficient in the art, such catalysts give satisfactory results. Thus they are used generally in an amount of 0.1–10 parts by weight, preferably in an amount of 0.2–1 part by weight, per 100 parts by weight of the compound (II).

The so-far known basic catalysts are also useful in conducting the ester exchange reaction step and include, among others, alkali or alkaline earth metal hydrides, such as sodium hydride and calcium hydride; alkali metal lower alkoxides, such as sodium methoxide and potassium tertbutoxide; metallic sodium and metallic potassium. When used in amounts known to be sufficient in the art, such catalysts can give satisfactory results. Thus they are used generally in an amount of 0.4–8 parts by weight, preferably in an amount of 0.8–5 parts by weight, per 100 parts by weight of the compound (II).

The ester exchange reaction step according to the invention is preferably conducted in a solvent. Usable solvents are, for example, toluene, xylene, heptane, tetralin, dimethyl sulfoxide, dimethylformamide, tetrahydrofuran, dioxane, diglyme, dimethylacetamide, hexamethylphosphoramide, 1,2-dimethoxyethane, acetonitrile and tertbutanol. Among them, toluene and xylene are preferred. The amount of the solvent is generally at most 5 parts by weight, preferably 0.1–1 part by weight, per part by weight of the compound (II).

The ester exchange reaction is conducted until substantial cessation of the alcohol formation resulting from the reaction of the compounds (II) and (III) with pentaerythritol. Generally, the reaction is conducted at a temperature of 80°–180° C. for 5–20 hours. The alcohol formed in this step is preferably removed instantaneously from the reaction system by a conventional method generally employed in carrying out various ester exchange reactions, for example by distilling off under reduced pressure (e.g. 5–50 mmHg).

The thus-produced tetrakis[3-(3,5-di-tert-butyl-4-hydroxyphenyl)propionyloxymethyl]methane is recrystallized in the conventional manner, preferably from a lower alkanol, more preferably from methanol.

The method of the invention is characterized by the possibility that pure crystalline products having a very good flowability can be obtained in very high yields.

EXAMPLES

The following examples are further illustrative of the invention but are by no means limitative thereof.

EXAMPLE 1

A one-liter reactor was charged with 418 g of methyl 3-(3,5-di-tert-butyl-4-hydroxyphenyl)propionate (hereinafter, "methyl ester"), 2.1 g of methyl 3-(3-tert-butyl-4-hydroxyphenyl)propionate (hereinafter, "monobutyl compound"), 44.2 g of pentaerythritol, 2.0 g of dibutyltin oxide and 300 g of toluene. The mixture was heated to 170°–175° C. with stirring. The byproduct methanol and the solvent toluene began to distill into a receptacle. The reaction was continued at 170°–175° C. for 10 hours while toluene (solvent) was supplemented to compensate the loss due to collection of the distilled toluene in the receptacle together with the methanol. Thereafter, 300 g of toluene, 2.0 g of oxalic acid and 12 g of powdered cellulose (Solka Floc) were added, and the mixture was heated under reflux for dehydration for 2 hours. The resultant oxalate salt of dibutyltin oxide was filtered off, the toluene was then distilled off under reduced pressure, 1,000 g of methanol (containing about 5% by weight of water) was added to the yellow glassy residue, the mixture was heated at 65° C. for dissolution and then cooled to room temperature, and the resultant crystals were collected by filtration and dried to give 343.4 g (yield: 90.0% of the theoretical) of tetrakis[3-(3,5-di-tert-butyl-4-hydroxyphenyl)propionyloxymethyl]methane. Melting point 113°–115° C.

EXAMPLES 2 and 3

The procedure of Example 1 was followed using varied amounts of the methy ester and monobutyl compound as shown in Table 1

TABLE 1

| | Methyl ester | Monobutyl compound | Yield | Melting point |
|---|---|---|---|---|
| Example 2 | 419 g | 1.05 g | 92.0% | 113–115° C. |
| Example 3 | 416 g | 4.2 g | 89.0% | 113–115° C. |
| Comparative Example 1 | 420 g | 0 g | 92.0% | 122–124° C. |

COMPARATIVE EXAMPLE 1

The procedure of Example 1 was followed without using the monobutyl compound for the reaction.

The results of the compound (I) are shown in Table 1 in terms of the production yield and melting point, together with the results obtained in Examples 1 to 3.

According to the method of the invention, tetrakis[3-(3,5-di-tert-butyl-4-hydroxyphenyl)propionyloxymethyl]methane, which is in wide use as an antioxidant for polyolefins can be obtained in high yields as fine granules having good properties without coloration, with certainty and good reproducibility.

The present invention has been described in detail in the foregoing specification including Examples, which can be modified and varied to such an extent as not to conflict with the concept and the scope of the present invention.

What is claimed is:

1. A method of producing tetrakis[3-(3,5-di-tert-butyl4-hydroxyphenyl)propionyloxymethyl]methane by ester exchange between a 3-(3,5-di-tert-butyl-4-hydroxyphenyl)propionic acid alkyl ester and pentaerythritol in the presence of a basic catalyst, which comprises carrying out the reaction in the presence of a 3-(3-tert-butyl-4-hydroxyphenyl)propionic acid alkyl ester.

2. The method of claim 1, wherein the ester exchange reaction is carried out in the presence of 0.1–5.0% by weight, relative to the 3-(3,5-di-tert-butyl-4-hydroxyphenyl)propionic acid alkyl ester, of said 3-(3-tert-butyl-4-hydroxyphenyl)propionic acid alkyl ester.

3. The method of claim 1, wherein the ester exchange reaction is carried out in the presence of 0.1–10% by weight, relative to the 3-(3,5-di-tert-butyl-4-hydroxyphenyl)propionic acid alkyl ester, of an organotin compound as a catalyst.

4. The method of claim 2, wherein the ester exchange reaction is carried out in the presence of 0.1–10% by weight, relative to the 3-(3,5-di-tert-butyl-4-hydroxyphenyl)propionic acid alkyl ester, of an organotin compound as a catalyst.

* * * * *